United States Patent
Moh et al.

(10) Patent No.: US 10,240,143 B2
(45) Date of Patent: Mar. 26, 2019

(54) RADIOFREQUENCY DEVICE FOR INCREASING INTRACELLULAR BIOACTIVE SUBSTANCE AND PLANT CELL CULTURE METHOD USING THE SAME

(71) Applicant: BIO-FD&C Co., LTD, Incheon (KR)

(72) Inventors: Sang-Hyun Moh, Yongin-si (KR); Jeong-Hun Lee, Seoul (KR); Hyo-Hyun Seo, Incheon (KR); Dong-Sun Shin, Incheon (KR); Moon-Jin Cho, Incheon (KR); Hyo-Seok Kang, Bucheon-si (KR); Hae-Soo Jung, Asan-si (KR); Hyun-Jin Oh, Suwon-si (KR); Yeong-Wook Yu, Yongin-si (KR); Ji-Hong Moh, Jinju (KR); Mun-Seong Heo, Seoul (KR); Ser-Jong Yoo, Seoul (KR); Hyun-E Lee, Incheon (KR); Jin-Hyeong Lee, Incheon (KR); Yu-Ri Lee, Incheon (KR); Eun-Ae Kim, Incheon (KR); Seung-Jun Lee, Jinju-si (KR)

(73) Assignee: BIO-FD&C CO., LTD (KR)

( * ) Notice: Subject to any disclaimer, the term of this patent is extended or adjusted under 35 U.S.C. 154(b) by 395 days.

(21) Appl. No.: 15/227,886

(22) Filed: Aug. 3, 2016

(65) Prior Publication Data
US 2017/0029803 A1 Feb. 2, 2017

Related U.S. Application Data

(62) Division of application No. 14/076,139, filed on Nov. 8, 2013, now Pat. No. 9,464,282.

(30) Foreign Application Priority Data

Nov. 9, 2012 (KR) .......................... 10-2012-0127017

(51) Int. Cl.
*C12M 3/00* (2006.01)
*C12M 1/00* (2006.01)
(Continued)

(52) U.S. Cl.
CPC ............. *C12N 13/00* (2013.01); *A01H 4/001* (2013.01); *C12M 35/04* (2013.01); *C12N 5/04* (2013.01); *C12N 2527/00* (2013.01)

(58) Field of Classification Search
CPC ....... C12M 35/00; C12M 35/02; C12M 35/06
See application file for complete search history.

(56) References Cited

U.S. PATENT DOCUMENTS 6,054,319 A * 4/2000 Worden ................. C12M 23/06
210/695
6,803,499 B1 * 10/2004 Anderson ................ A01H 4/00
800/281

(Continued)

FOREIGN PATENT DOCUMENTS

| KR | 100193201 | 2/1999 |
| KR | 1020010094111 A | 10/2001 |
| KR | 100842420 B1 | 6/2008 |

*Primary Examiner* — Nathan A Bowers
(74) *Attorney, Agent, or Firm* — JHK Law; Joseph Hyosuk Kim

(57) ABSTRACT

There are provided a radiofrequency device for increasing amount of a bioactive substance in a plant cell and a plant cell culture method for increasing amount of useful intracellular secondary metabolites by using the radiofrequency device. The cell culture method of the present invention makes it possible to increase specific secondary metabolites such as daidzein, equol, and the like in a cell and thus can be used for development into various medicines, agricultural pesticides, spices, pigments, food additives, and cosmetics containing bioactive substances. Further, the cell culture method of the present invention improves conventional cell culture methods limitedly used for specific cells or specific (Continued)

metabolites for increasing amount of intracellular bioactive substances and thus can be widely applied to production of cells and secondary metabolites.

4 Claims, 8 Drawing Sheets

(51) Int. Cl.
*C12N 13/00* (2006.01)
*C12N 5/04* (2006.01)
*A01H 4/00* (2006.01)
*C12M 1/42* (2006.01)

(56) References Cited

U.S. PATENT DOCUMENTS

2005/0153437 A1 7/2005 Kishida et al.
2006/0223155 A1 10/2006 Streeter

* cited by examiner

RADIOFREQUENCY DEVICE FOR INCREASING INTRACELLULAR BIOACTIVE SUBSTANCE AND PLANT CELL CULTURE METHOD USING THE SAME

FIELD OF THE INVENTION

The present invention relates to a radiofrequency device for increasing amount of a bioactive substance in a plant cell and a plant cell culture method for increasing amount of useful secondary metabolites in the plant cell by using the radiofrequency device.

BACKGROUND OF THE INVENTION

Plants are useful resources for producing a wide range of secondary metabolites to be used for medicines, agricultural pesticides, spices, pigments, food additives, cosmetics, etc. However, if a secondary metabolite is directly extracted from a plant, its content is low, and its productivity is highly varied depending on a cultivation condition or a part of the plant, which causes an unstable supply of the secondary metabolite. Further, while demands for secondary metabolites are increased in food, medicine, and cosmetic fields, supplies of secondary metabolites directly produced by cell culture are still limited. In order to solve such a problem, there have been various attempts to control a mass production process and a culture condition in a bio reactor capable of mass-producing secondary metabolites.

Mass production of secondary metabolites through plant cell culture has problems of instability of a culture cell strain, low productivity, and slow growth, mass culture, and the like. In order to overcome the problem of low productivity, conventionally, 1) manipulation of nutriments of a culture medium such as addition of sugars, nitrates, phosphates, growth regulators, and precursors, or the like, 2) optimization of culture environment such as a culture temperature, lighting, acidity of a medium, etc., 3) treatment of derivatives for increasing productivity, 4) cell membrane permeabilization and two-phase culture for effectively collecting of secondary metabolites, and 5) modification of genes involving biosynthesis of secondary metabolites and transfer of exotic genes have been used for increasing productivity of secondary metabolites. However, such methods can be limitedly used for specific cells or specific metabolites but cannot be generally applied to cell culture and secondary metabolites.

Meanwhile, a method for culturing cells is classified into a batch culture method in which a culture fluid and a cell are supplied once at the beginning and there is no more supply or removal of nutriments, and a continuous culture method in which a culture fluid is put in an incubator and a new culture fluid is supplied from the outside at a constant speed while the old culture fluid containing a cultured product is discharged to the outside at the same speed so as to continuously culture cells without lack of nutrients. The batch culture method is not suitable for mass production. Therefore, as one of the continuous culture methods, a perfusion culture method in which a cell is left in an incubator and a medium containing a product is continuously collected while a new medium is supplied has attracted attention. In this case, it is disclosed that cells and a medium are separated from each other by using ultrasonic waves. To be specific, by using an ultrasonic cell separator operated such that when cells start to be discharged to the outside of the cell separator after ultrasonic waves are irradiated, the irradiation of the ultrasonic waves is stopped, and the cells are returned to a bio reactor by applying a counter pressure with a pump, and then the ultrasonic waves are irradiated again, the cells and the medium are separated, whereby plant cells are cultured at a high density. However, in this case, the ultrasonic waves are used to separate the cells and the medium, but cannot much contribute to an increase in content of secondary metabolites of the cells. Further, it has been pointed out that necrosis of the plant cells is often caused by the ultrasonic waves.

Patent Document 1: Korean Patent Application No. 10-1997-0008119

Patent Document 2: Korean Patent Application No. 10-2000-0017570

BRIEF SUMMARY OF THE INVENTION

An object of the present invention is to provide a cell culture method for increasing amount of a bioactive substance in a plant cell.

Further, another object of the present invention is to provide an optimum condition of radiofrequency process intensity, a processing method, and the like for increasing amount of an intracellular bioactive substance.

Furthermore, still another object of the present invention is to provide a radiofrequency device for increasing amount of an intracellular bioactive substance.

In order to achieve the above objects, an exemplary embodiment of the present invention provides a cell culture method for increasing amount of a bioactive substance in a plant cell, the method comprising: (a) a culturing step of inoculating the plant cell into a medium and culturing the plant cell; and (b) a radiofrequency processing step of processing the cultured cell with a radiofrequency for increasing amount of a bioactive substance in the plant cell.

In an example of the present invention, the radiofrequency may be used for process in a range of 0.1 to 15 MHz.

In an example of the present invention, the culturing step may further comprise: (a1) a callus inducing step of culturing the plant cell in an MS medium containing IAA (indole acetic acid), BAP (6-benzylaminopurine), sucrose, and gelite for 2 to 5 weeks for inducing a callus from the germinated plant; and (a2) an adventitious root inducing step of culturing the callus in an MS medium containing IBA (indole-3-butyric acid), MES monohydrate(2-(N-morpholino), benzyladenine, sucrose, and gelite for 2 to 5 weeks for inducing an adventitious root from the callus.

In an example of the present invention, the radiofrequency may be used for process 3 times every 2 to 10 minutes per day repeatedly for 5 to 15 days.

In an example of the present invention, the bioactive substance may be at least one secondary metabolite selected from the group consisting of alkaloids, flavonoids, terpenenoids, glycosides, and metabolite pigments.

In an example of the present invention, the flavonoid as a secondary metabolite may be at least one metabolite selected from the group consisting of isoflavones, flavonols, flavanones, flavones, flavan-3-ols, and anthocyanins.

In an example of the present invention, the isoflavone may be at least one secondary metabolite selected from the group consisting of daidzein, genistein, and equol.

Further, the present invention provides a radiofrequency cell incubator comprising: a bio reactor configured to culture a plant cell accommodated therein by supplying a radiofrequency and air; a radiofrequency supplier configured to supply a radiofrequency to the bio reactor for increasing amount of an intracellular bioactive substance; an air supplier configured to supply air to the bio reactor; and an oscillograph connected to the radiofrequency supplier and configured to record vibration of the bio reactor.

In an example of the present invention, the bio reactor may include a case in which an inlet opening for supplying a cell culture and a culture fluid is provided at an upper part, radiofrequency installation units are aligned at both sides in the same line, and an air inlet opening is provided at a lower part; an upper cover configured to open or close the inlet opening; radiofrequency terminals installed at the respective radiofrequency installation units and configured to transmit a radiofrequency transmitted from the radiofrequency supplier; a horizontal supporting plate formed in a plate shape and including fixing holes for supporting the case in the center; and fixing rods vertically installed under the horizontal supporting plate along a periphery of the horizontal supporting plate.

In an example of the present invention, buffer members may be installed at connection portions between the case and the horizontal supporting plate and between the horizontal supporting plate and the fixing rods, respectively, to reduce shock and vibration.

DETAILED DESCRIPTION OF THE INVENTION

Figure 1A:
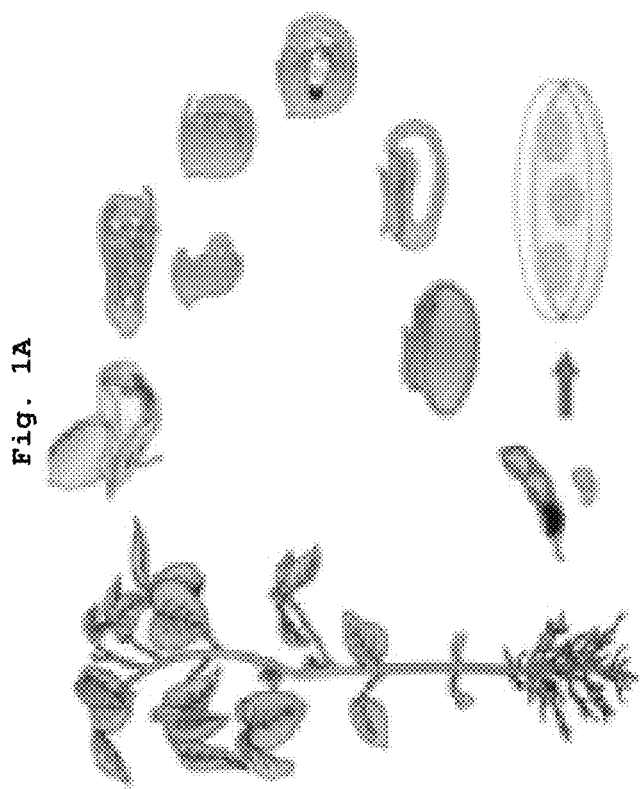
FIG. 1A is a schematic diagram showing a method for inducing calluses from a plant.

The present invention relates to a radiofrequency device for increasing amount of an intracellular bioactive substance and a cell culture method for increasing amount of useful secondary metabolites in a cell by using the radiofrequency device.

Secondary metabolites refer to natural products that do not have primary and direct physiological functions, such as growth, development, and reproduction of an organism, required for survival and are limitedly produced by specific organisms.

The secondary metabolites are mainly produced by plants and microorganisms, and it is not too much to say that most of major and useful metabolites are derived from plants and microorganisms. Unlike plants, animals are different in terms of genetic composition, nutrition supply source, and storage type, and they have mobility and thus can easily obtain food required for daily life and also can avoid danger threatening life. Meanwhile, in the case of plants without mobility, they protect themselves by producing toxic substances as a measure of self-defense and generate secondary metabolites as a means to lure insects for nutrition competition or propagation of species.

Conventionally, a technology for analyzing and extracting such secondary metabolites was not developed and plants containing useful substances were searched by using five senses. However, recently, along with development of natural product chemistry, biology, pharmacology, and biochemistry, analysis methods have been developed, so that it is possible to accurately extract a trace of a substance and also possible to determine a structure thereof. Along with this trend, there has been conducted research focusing on a method for producing more various secondary metabolites in more amounts based on usability of secondary metabolites.

Synthesis and accumulation of secondary metabolites may be often carried out limitedly at a specific time in specific organs, tissues, or cells. Thus, it is important to catch such an appropriate time and extract sufficient secondary metabolites. Currently, production of secondary metabolites depends largely on cell culture. This is because cell culture exhibits a high growth rate as compared with an organism and is not influenced by local and climatic restrictions and less damaged by disease and insects through sterile culture, whereby it is possible to carry out uniform culture regardless of environmental conditions. Further, cell culture can be carried out under an environment artificially regulated to promote production of specific secondary metabolites.

Secondary metabolites can be classified into four kinds, i.e. alkaloids, phenol compounds, terpenes, and other metabolites, depending on a structure and a synthesis process.

Alkaloid is an aromatic nitrogen compound and has a heterocyclic structure including a nitrogen atom. A molecule of the alkaloid is alkaline due to the positively charged nitrogen atom and generally water-soluble. The alkaloids can be classified into several kinds, i.e. pyrrolidine, tropane, piperidine, pyrrolizidine, quinolizidine, isoquinoline, indole, etc., depending on a structure of a heterocycle. There have been found about 100,000 or more kinds of alkaloids accounting for 20 to 30% of vascular plants and mostly distributed in plants. Most of them are found from herbaceous dicotyledones, and it is known that a plant such as poppy or cinchona contains 20 or more kinds of alkaloids. Although functions of alkaloids in plants are not known, the alkaloids have attracted lots of attention due to their strong physiological effects on animals including mammals. Nicotine, caffeine, cocaine, and the like have a function of a stimulant or a sedative and thus have been widely used as favorite foods. Morphine, codeine, atropine, ephedrine, quinine, and the like have been usefully used as medicines.

Meanwhile, a phenol compound is a generic term for secondary metabolites having an aromatic cyclic structure including a substitutable hydroxyl group. A phenol compound of a plant includes chemically heterogeneous substances some of which are dissolved in an organic solvent only and some of which are water-soluble carboxyl acids, glycosides, and macro polymers. A function of the phenol compound is as varied as a structure thereof and includes a defense function against attack of an herbivore or a pathogen, a mechanical supporting function, a function of inducing pollination vectors and dispersing seeds, a function of inhibiting growth and development of adjacent competitor plants.

The phenol compounds include flavonoids. There are many kinds of flavonoids which can be classified into four kinds, i.e. anthocyanins, flavones, flavonoles, and isoflavones, depending on a structure and a position of a substituent.

The anthocyanins are pigments found in red, pale pink, purple, and blue fruit and flowers and capable of luring animals to spread pollen and seeds, and it is known that the anthocyanins can improve functions of eyes and liver.

The flavones and flavonoles can be found in flowers and generally absorb light having a shorter wavelength as compared with the anthocyanins. Therefore, these pigments are invisible to the human eye but visible to insects such as bees capable of seeing ultraviolet rays.

The isoflavones have structural similarities and functional similarities to estrogens and have effects of the estrogens in the body as one of phytoestrogens. Therefore, it is reported that the isoflavones have the effect of preventing osteoporosis, cancer, cardiovascular diseases, and the like. If the estrogens are used for a long time, they may cause side effects of a risk of developing cancer, headache, and the like, which is now being debated. Meanwhile, the isoflavones act as agonists or antagonists depending on a bonding ability of an estrogen receptor but side effects thereof have rarely been reported. The Food and Drug Administration recommends intake of 25 mg or more of isoflavones per day.

Daidzein is one of isoflavone compounds separated from a soybean. It is known that the daidzein works to lower blood cholesterol and thus it is effective in preventing and treating for various chronic diseases. The daidzein has a structure similar to that of estrogen, and, thus, an internal absorption rate thereof is high. The daidzein is activated by being bonded to an estrogen receptor. As compared with estrogen therapy causing side effects such as breast cancer, the daidzein has no side effect, and, thus, it has attracted attention as an alternative substance to the estrogen. It is known as a highly effective antioxidant capable of reducing damage caused by free radicals in tissue, and it serves as a dietary supplement formulation effective for menopausal women through a function similar to that of the estrogen. Further, regarding cancer cell growth in the body, the daidzein can be used as a material for controlling random growth of cells and appropriately regulating cell growth and cell division.

<Chemical Formula of Daidzein>

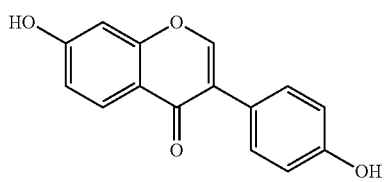

Meanwhile, equol is known as a metabolite of the daidzein. It is reported that the equol inhibits DHT (dihydrotestosterone) as a male hormone causing prostate cancer and male pattern baldness. That is, it was confirmed that when the equol was injected into a male mouse, prostate became small. Further, when DHT was injected into a mouse incapable of generating the DHT due to removal of its testicles, prostate of the mouse became large, but it was confirmed that in the case of injecting the equol together, such a change was not observed.

<Chemical Formula of Equol>

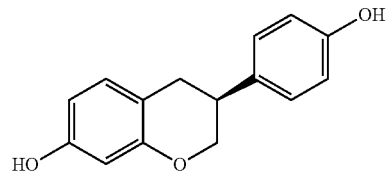

Further, the terpenes have the greatest diversity among secondary metabolites and are known as having an insecticidal effect. Moreover, other secondary metabolites such as glycosides, glucosinolates, canavanines, etc. have been known.

The present inventors conducted research on plant cells for culturing cells containing high levels of useful secondary metabolites.

Above all, the present inventors induced a callus by using a soybean placenta for culturing cells derived from plants and induced an adventitious root from the callus. The term "callus" means tissue formed when a plant body is wounded and tissue formed at the wounded part of the plant body, and mainly refers to amorphous tissue or mass of cells formed by culturing segments, organs, tissues, or the like and losing ability to cause of normal organogenesis or histodifferention. The callus is mostly comprised of parenchyma cells and can be a common name for plant tumor tissues formed by infection of agrobacterium or the like in a broad sense Nowadays, the callus refers to specific tissue or mass of cells formed when tissue cut off from a plant body is cultured in a medium containing auxin, when a certain kind of a plant is wounded, or when a wounded part is treated with auxin. The callus is undifferentiated plastid and can be differentiated into various organs such as stems, roots, and leaves by various stimuli. Thus, it is sometimes referred to as a stem cell.

The callus becomes a useful means for tissue culture. The term "tissue culture" means a technology in which a callus is formed by culturing an organ, a tissue, or a cell separated from a plant in an artificial medium containing nutrients to maintain, differentiate, and proliferate a plant body. Unlike an animal cell, a plant cell has a totipotency (ability of a cell or tissue to form a shape of the whole cell or to reproduce a plant body and to be differentiated into all of cells) as an ability to be differentiated into all of cells, which enables such tissue culture.

According to plant tissue culture, an organ, a tissue, or a cell of a plant comprised of lots of cells is extracted and separated from a plant body and cultured in a reactor containing nutrients to induce a callus or a group of single cells or to redifferentiate the plant body or organ into a plant body in the callus or the cell.

A callus can be generated at any one part of leaves, stems, roots, etc. through such tissue culture, and a callus can be continuously generated by subculture. Further, by repeating proliferation of a completely undifferentiated cell and regulating an amount of a plant hormone in a medium, an irregular vessel or phloem can be differentiated, an adventitious bud or an adventitious root can be formed, and an intact individual can be formed at the callus. Therefore, the callus is a key material for research on formation of a shape.

The present inventors generated a callus at a soybean placenta and induced an adventitious root from the callus and then tissue-cultured the adventitious root by using a radiofrequency cell incubator 100. That is, the present inventors tried to increase secondary metabolites as useful intracellular substances by carrying out a tissue culture step with a radiofrequency.

The tissue culture can be carried out in a bio reactor of the radiofrequency cell incubator 100. The bio reactor refers to an apparatus used for producing substances by using a characteristic of an enzyme capable of effectively regulating a high specificity reaction at normal temperature and pressure. Although the bio reactor originally refers to an apparatus for culturing a microorganism or a cell to produce substances by using a reaction of living body, it often refers to a reactor allowing various chemical reactions to be carried out by using an immobilized enzyme or a microorganism and has been used to mass-produce useful substances on an industrial scale or to diagnose a disease through microdetermination of a specific biogenic substance. Unlike a conventional culture method in which a solid medium prepared is explanted in each bottle, in the case of the bio reactor, a large amount of a liquid medium is put into the reactor and cultured while air is supplied into the reactor. Therefore, with the bio reactor, as compared with the conventional culture method, culture can be carried out in a large amount at the same time along with excellent growth, and, thus, excellent shoots can be obtained in a much shorter time. Further, the bio reactor has been used to extract main substances from a plant. In the present invention, there has been used a bio reactor equipped with a radiofrequency supplier for particularly increasing amount of intracellular secondary metabolites, and a configuration thereof will be described in detail below.

The radiofrequency cell incubator 100 as the present invention is comprised of a bio reactor 200, a radiofrequency supplier configured to supply a radiofrequency to the bio reactor 200, an air supplier 400 configured to supply air to the bio reactor 200, and an oscillograph 500 connected to the radiofrequency supplier 300 and configured to record vibration of the bio reactor 200.

The bio reactor 200 is configured to culture a cell culture accommodated therein by supplying a radiofrequency and air thereto.

The bio reactor 200 carried out as described above is comprised of a case 210 having a predetermined size, an upper cover 220 detachably provided at an upper part of the case 210, radiofrequency terminals 230 aligned at both sides of the case 210 in the same line, a horizontal supporting plate 240 supporting the case 210, and fixing rods 250 having a predetermined height and supporting the horizontal supporting plate 240.

Further, in the case 210, an inlet opening 211 for supplying a cell culture and a culture fluid is provided at an upper part, radiofrequency installation units 212 are aligned at both sides in the same line, and an air inlet opening 213 is provided at a lower part.

That is, the case 210 is formed in an upside-down gourd bottle shape, and the inside thereof communicates with the inlet opening 211, the radiofrequency installation units 212, and the air inlet opening 213 provided at the upper part, the both sides in the same line, and the lower part, respectively.

Furthermore, the upper cover 220 detachably provided at the upper part of the case 210 opens or closes the inside of the case 210 by locking or unlocking.

Then, the radiofrequency terminals 230 respectively provided at the radiofrequency installation units 212 constituting the case 210 transmit a radiofrequency transmitted from the radiofrequency supplier 300 to the inside of the case 210.

Further, in the present invention, the radiofrequency terminal 230 is comprised of a terminal portion 231 formed in "┤" shape, a sealing member 232 provided at one side of the terminal portion 231 and tight on the radiofrequency installation unit 212 of the case 210, and a connection line 233 of which one side is connected to the terminal portion 231 and the other side is connected to the radiofrequency supplier 300.

That is, the radiofrequency terminal 230 is configured to receive a radiofrequency through the connection line 233 connected to the radiofrequency supplier 300 and propagate the radiofrequency into the case 210 thorough the terminal portion 231.

Furthermore, the horizontal supporting plate 240 supporting the case 210 is manufactured into a plate having predetermined thickness and diameter and includes fixing holes 241 for fixing the case 210 in the center.

Moreover, fixing rods 250 vertically installed under the horizontal supporting plate 240 along a periphery of the horizontal supporting plate 240 may be formed of one selected from publicly known rods or bars having a predetermined height.

In this case, buffer members 260 made of a material selected from rubber, silicon, and synthetic resin are installed at connection portions between the case 210 and the horizontal supporting plate 240 and between the horizontal supporting plate 240 and the fixing rods 250, respectively, to reduce shock and vibration.

Herein, the buffer member 260 is formed in a hollow shape and may selectively include embossing projections at intervals at its upper and lower parts.

The radiofrequency supplier 300 comprised of an operation unit (not illustrated) configured to generate a radiofrequency, a manipulation unit 310 configured to regulate an on/off operation and a radiofrequency, a display unit 320 configured to display a current status and an operation status, and a level meter 330 configured to display a status of a frequency supplies a radiofrequency to the bio reactor 200.

Herein, the operation unit is formed of one selected from operation units constituting publicly known radiofrequency suppliers, and detailed explanation thereof will be omitted.

That is, the radiofrequency supplier 300 supplies a radiofrequency to the radiofrequency terminals 230 of the bio reactor 200 while the operation unit is operated in association with an operation of the manipulation unit 310, and a current status can be monitored in real time through the display unit 320 and the level meter 330.

The air supplier 400 has a predetermined size and includes an air generation unit (not illustrated) therein. Discharge openings 420 configured to discharge air are formed in front, and an air hose 440 configured to deliver air is installed at the discharge opening 420 so as to supply air to the bio reactor 200.

Herein, the air generation unit is formed of one selected from air generation units constituting publicly known air suppliers or air supplying devices, and detailed explanation thereof will be omitted.

That is, the air generation unit 400 generates air through the air generation unit in response to an input signal and supplies the air to the case 210 of the bio reactor 200 through the discharge opening 420 and the air hose 440.

The oscillograph 500 is comprised of a vibration operation unit (not illustrated) configured to convert and record vibration, a vibration manipulation unit 510 configured to regulate an on/off operation and various functions, a vibration display unit 520 configured to display a current status, and a connection line 530 connected to the radiofrequency supplier 300.

Herein, the vibration operation unit is formed of one selected from vibration operation units installed at publicly known oscillographs, and detailed explanation thereof will be omitted.

That is, the oscillograph 500 enables real-time monitoring of a vibration status of the bio reactor 200 through the connection line 530 connected to the radiofrequency supplier 300 and the vibration display unit 520.

An example of the radiofrequency cell incubator 100 configured as described above will be explained below.

Above all, the a case 210 having a predetermined size, the upper cover 220 detachably provided at an upper part of the case 210, the radiofrequency terminals 230 aligned at both sides of the case 210 in the same line, the horizontal supporting plate 240 supporting the case 210, and the fixing rods 250 having a predetermined height and supporting the horizontal supporting plate 240 are prepared.

Then, the radiofrequency supplier 300 comprised of the operation unit (not illustrated) configured to generate a radiofrequency, the manipulation unit 310 configured to regulate an on/off operation and a radiofrequency, the display unit 320 configured to display a current status and an operation status, and the level meter 330 configured to display a status of a frequency is installed at an interval with the bio reactor 200.

Thereafter, the air supplier 400 having a predetermined size and including an air generation unit (not illustrated) therein, the discharge openings 420 configured to discharge air and formed in front thereof, and the air hose 440 configured to deliver air and installed at the discharge opening 420 is installed at an interval with the radiofrequency supplier 300.

Then, when the oscillograph 500 comprised of the vibration operation unit (not illustrated) configured to convert and record vibration, the vibration manipulation unit 510 configured to regulate an on/off operation and various functions, the vibration display unit 520 configured to display a current status, and the connection line 530 connected to the radiofrequency supplier 300 is installed at one side of the air supplier 400, assembly of the radiofrequency cell incubator 100 is completed.

Herein, an assembly sequence of the radiofrequency cell incubator 100 may be different from the above-described sequence.

Hereinafter, a use state of the radiofrequency cell incubator 100 configured as described above will be explained below.

Above all, the upper cover 220 closing the inlet opening 211 of the case 210 constituting the bio reactor 200 is opened. Then, a culture fluid and a cell culture are supplied into the case 210 and the inlet opening 211 is closed by using the upper cover 220.

Further, a set value of a radiofrequency is regulated by using the manipulation unit 310 constituting the radiofrequency supplier 300. Then, the radiofrequency is supplied to the radiofrequency terminals 230 of the bio reactor 200 through the connection line 233.

At the same time, air generated by the air supplier 400 is supplied to the air inlet opening 213 of the bio reactor 200 through the air hose 440.

Thereafter, the cell culture accommodated within the case 210 is influenced by the radiofrequency transmitted through the radiofrequency terminals 230, and a user can monitor radiofrequency information supplied in real time through the display unit 320 and the level meter 330.

Furthermore, vibration of the bio reactor 200 transmitted to the radiofrequency supplier 300 is recorded by the oscillograph 500.

Hereinafter, there will be explained Examples of a cell culture method for increasing amount of bioactive substances by using the radiofrequency device. These Examples are provided for the purpose of illustration, but the scope of the present invention cannot be limited thereto.

EXAMPLE 1

Surface Disinfection of Cultured Tissue

The present inventors used a soybean placenta to culture a plant cell based on the idea that placenta tissue is tissue for forming seeds of a plant and various phytochemicals are expressed and a level of such expression is high. The placenta refers to tissue where an ovule is located in an ovary of a pistil, and the placenta is usually positioned at the edge of an carpel constituting the ovary and sometimes positioned at a medius of the carpel and may be formed in a straight pillar shape at a base of the ovary or from the base in the ovary.

The present inventors first carried out a disinfection process in order to induce a callus from the soybean placenta tissue. To do so, the soybean placenta was cut into appropriate-sized pieces, and a surface of the placenta was washed with running water for about 6 hours. The soybean placenta tissue clearly washed was immersed in 70% ethanol for 5 seconds for primary disinfection and then washed with sterile water 3 times and treated in a 4% NaOCl solution for 10 minutes for surface sterilization. Then, the soybean placenta tissue was washed with sterile water 3 times in a clean bench and moisture thereof was removed with sterile filter paper.

EXAMPLE 2

Induction of Callus

Figure 1B:
FIG. 1B provides photos showing induced calluses according to a desirable example of the present invention. (duplicate experiments)

The present inventors cut the washed soybean placenta tissue into pieces about 5 mm long about 5 mm wide. In order to induce calluses therefrom, the washed plant tissue was explanted and cultured in a MS (Murashige and Skoog) medium containing 2 mg/L of IAA (indole acetic acid) as one of auxins as plant growth regulators, 2 mg/L of BAP (6-benzylaminopurine) as one of cytokinins, 30 g/L of sucrose, and 2 g/L of gelite as an agar medium at 25±2° C. for 4 weeks. As a result, as can be seen from FIG. 1B, a callus was observed.

EXAMPLE 3

Induction of Adventitious Root

The present inventors induced an adventitious root by using the callus induced in Example 2. An adventitious root refers to a root which is not developed from an apical meristem derived from a seed but shown during cutting of a tree, cutting of a leaf, or tissue culture.

In order to culture the adventitious root, the present inventors explanted and cultured the callus in a MS (Murashige and Skoog) medium containing 2 mg/L of IBA (indole-3-butyric acid) as plant growth regulator, 0.5 g/L of MES Monohydrate(2-(N-morpholino) ethanesulfonic acid)), 2 mg/L of benzyladenine, 30 g/L of sucrose, and 2 g/L of gelite as an agar medium at 21±1° C. for 4 weeks. The culture was carried out at a pH of 5.8 in a dark room condition.

While culturing the adventitious root, the present inventors made it possible to produce a substance from which root initiation was inevitable for expression of biosynthesis.

EXAMPLE 4

Comparison of Bioactive Substances Induced by Radiofrequency Process

The present inventors tried to compare bioactive substances induced by performing a radiofrequency process onto the induced adventitious root. Above all, while culturing the adventitious root in the radiofrequency cell incubator, the present inventors applied a radiofrequency of 240 kHz or 270 kHz to the adventitious root 3 times every 5 minutes for a day and repeated this process for a week or two weeks. A reaction volume of a bio reactor was 1 L, power was 20 W, and a cell culture medium contained 4.4 g of MS medium powder, 30 g of sucrose, 2 mg of benzyl adenine, 2 mg of IAA, and MES (pH 5.8) for buffering.

The sample cultured in the medium for a week with a radiofrequency process was collected and vacuum-dried for 6 to 10 hours. Then, the sample was ultrasonic extracted with 50% ethanol as a solvent for 1 hour and vortexed for 30 minutes. When secondary metabolites were sufficiently released to a supernatant, the supernatant was obtained by centrifugation. All samples were analyzed by using an HPLC (HPLC (Waters 650E Advanced Protein Purification System) and Gemini 5 u C18 110 A (4.6×250 mm, 5 micron, Phenomenex Co., Ltd.) was used as a column. While the analysis was carried out, a concentration gradient of water (containing 0.1% TFA (Trifluoro acetic acid)):acetonitrile (containing 0.1% TFA (Trifluoro acetic acid)) in a mobile phase solvent was changed from 10:0 in initial 0 to 45 minutes to 1:9 in a time range of 45 to 50 minutes and a flow rate was 1 ml/min. A UV detector (230 nm) was used as a detector.

Figure 2:
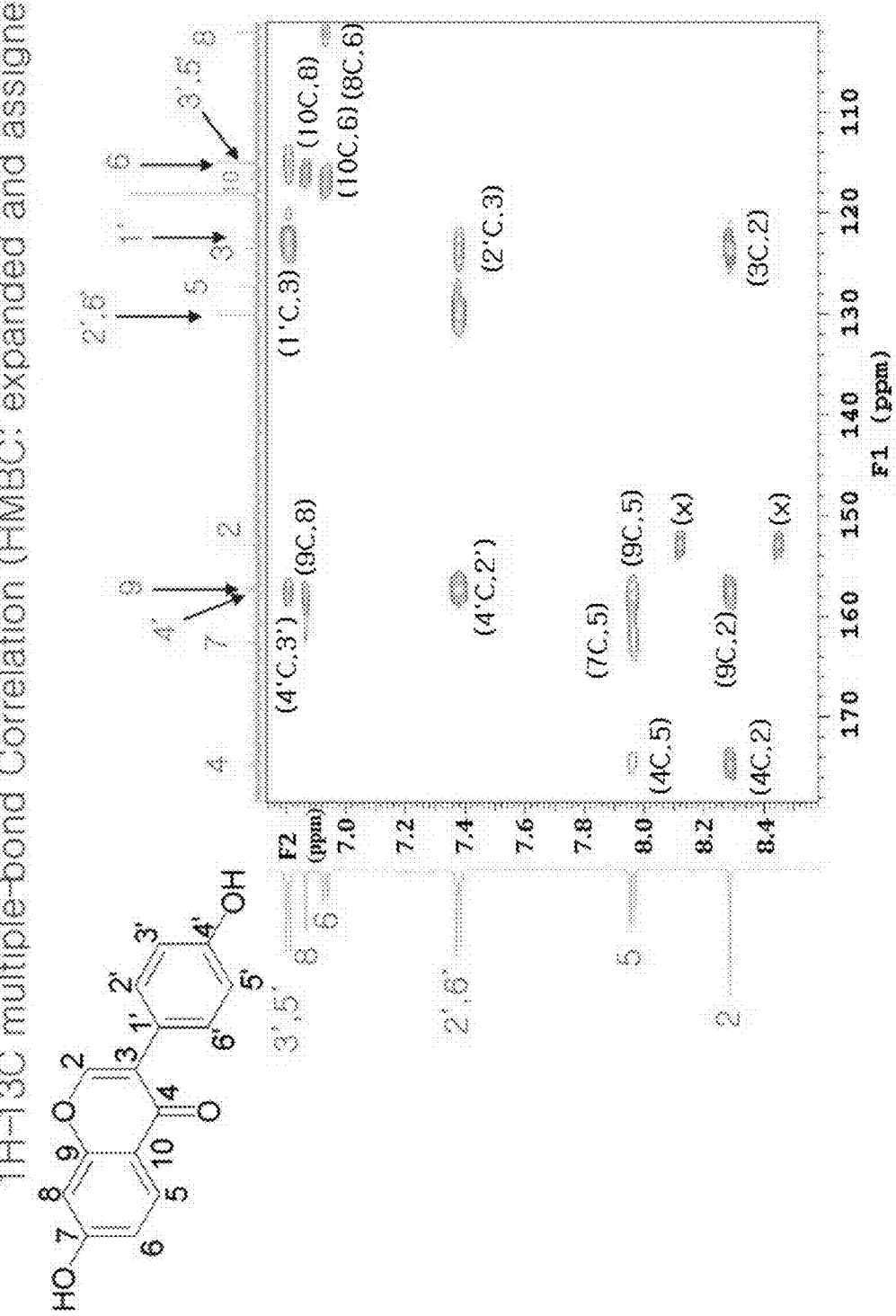
FIG. 2 shows an HPLC result obtained by identifying a substance increased during a radiofrequency process onto a plant cell.
Figure 3:
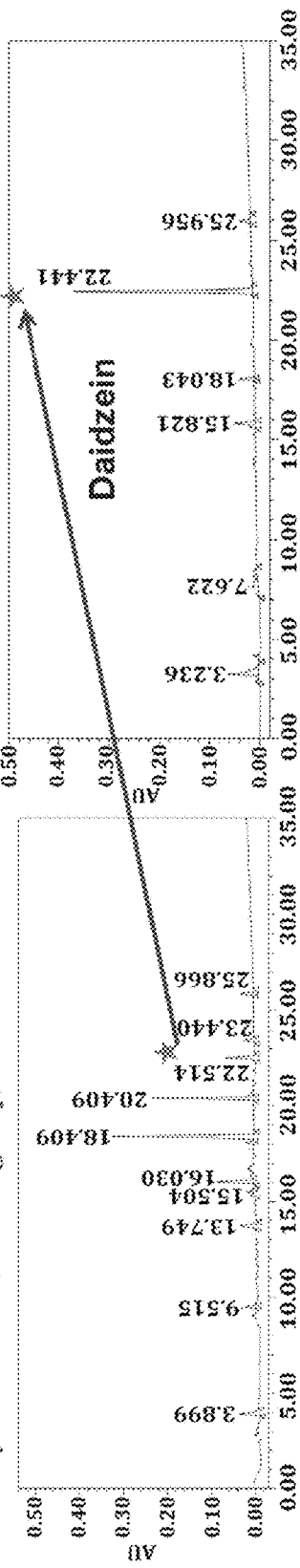
FIG. 3 is a graph showing that daidzein is increased during a radiofrequency process onto a plant cell.
Figure 4:
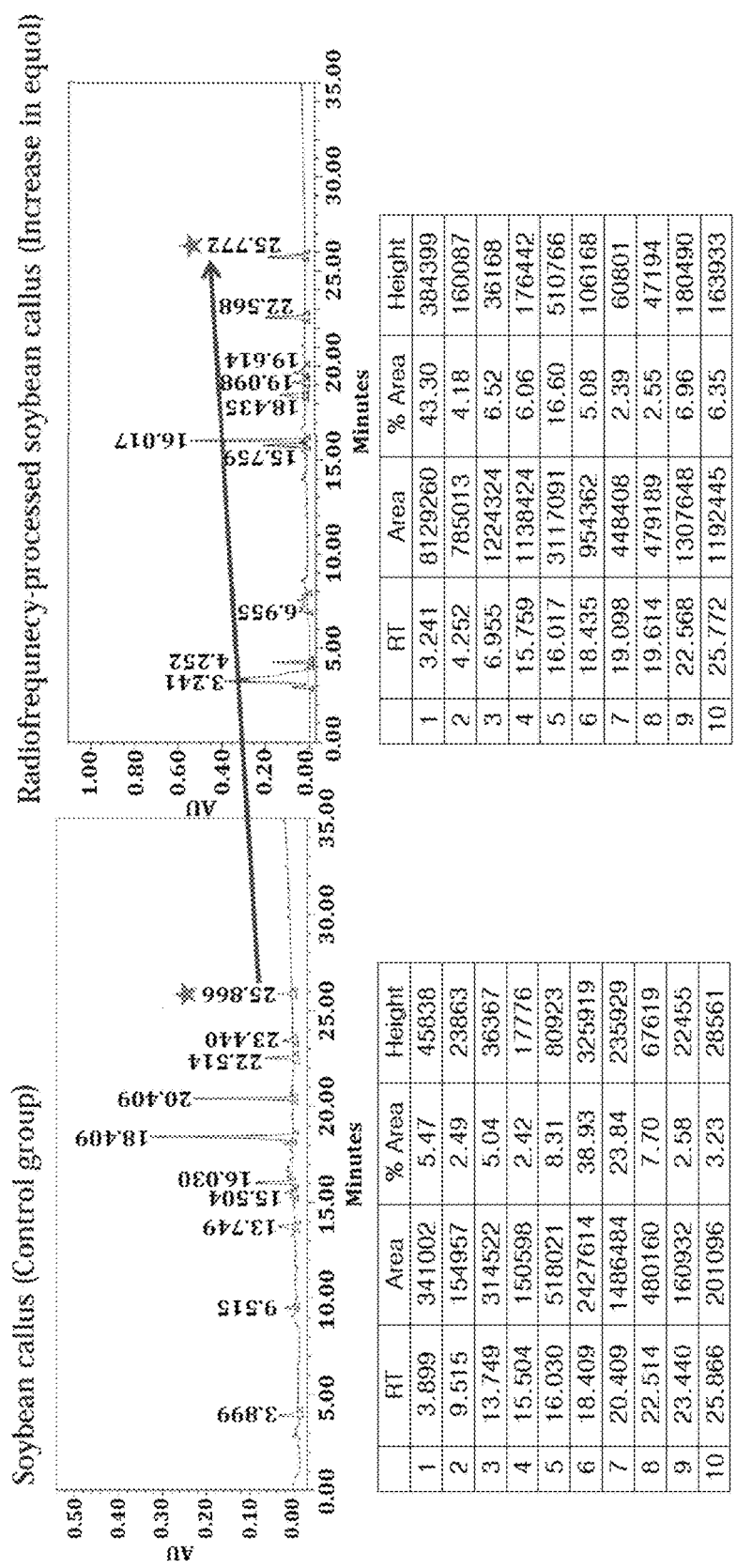
FIG. 4 is a graph showing that equol is increased during a radiofrequency process onto a plant cell.
Figure 5:
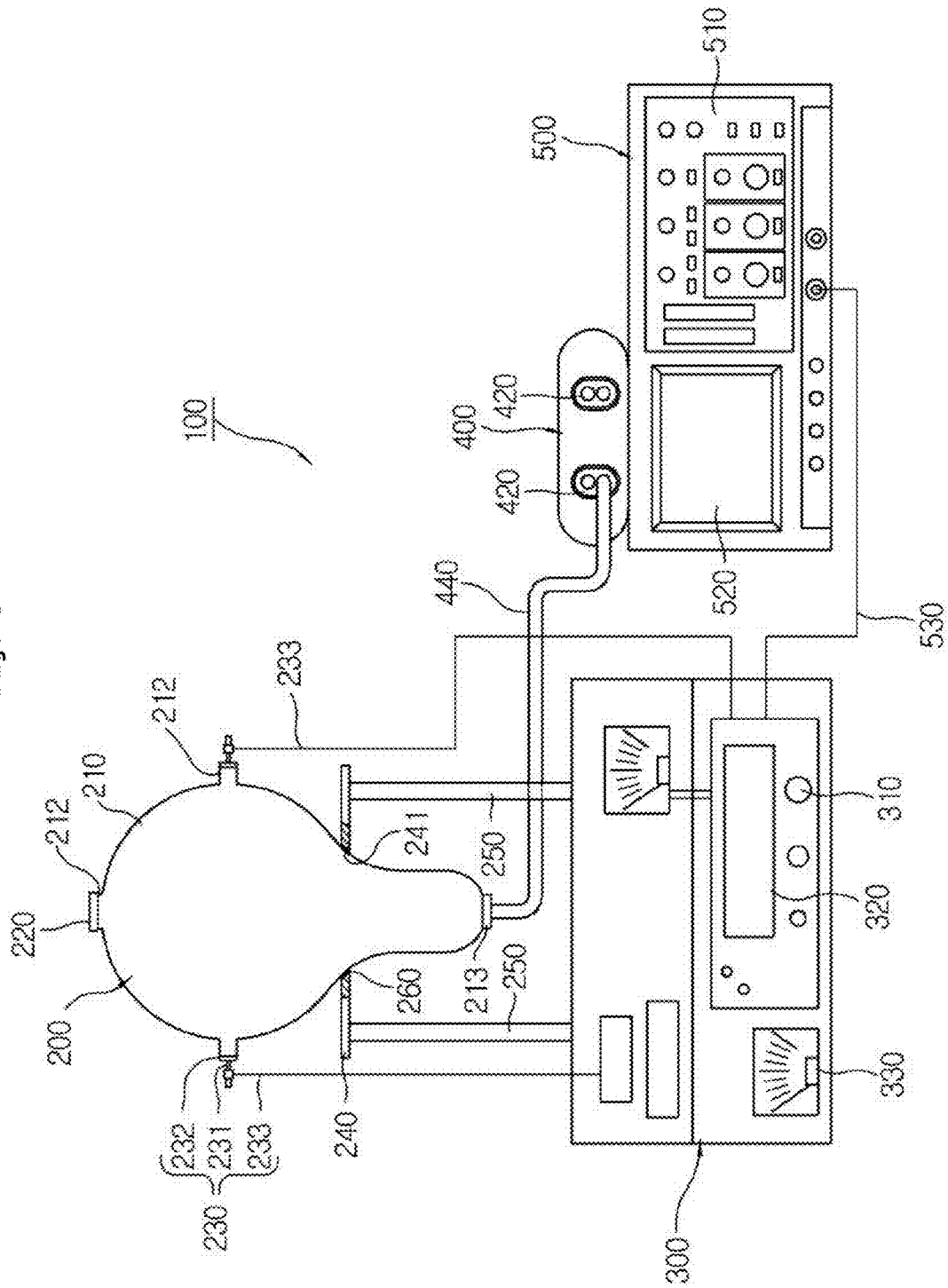
FIG. 5 is a configuration view showing a radiofrequency cell incubator according to the present invention.
Figure 6:
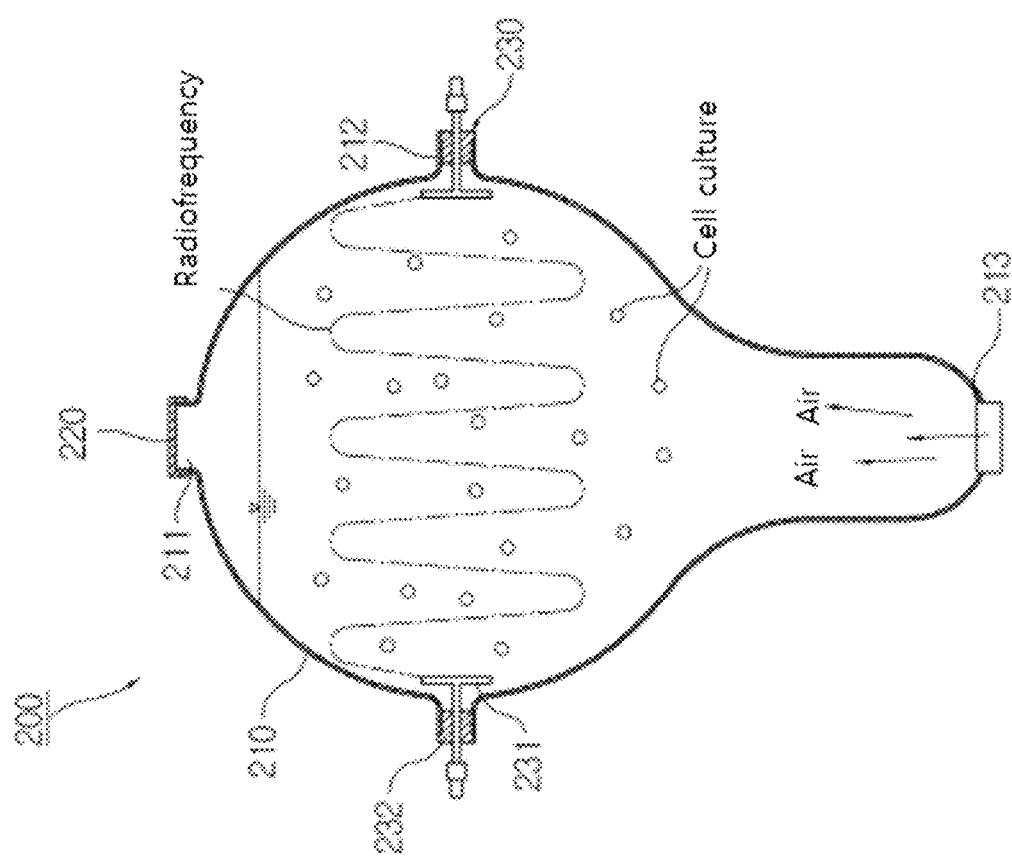
FIG. 6 is a cross-sectional view showing a bio reactor constituting a radiofrequency cell incubator according to the present invention.
Figure 7:
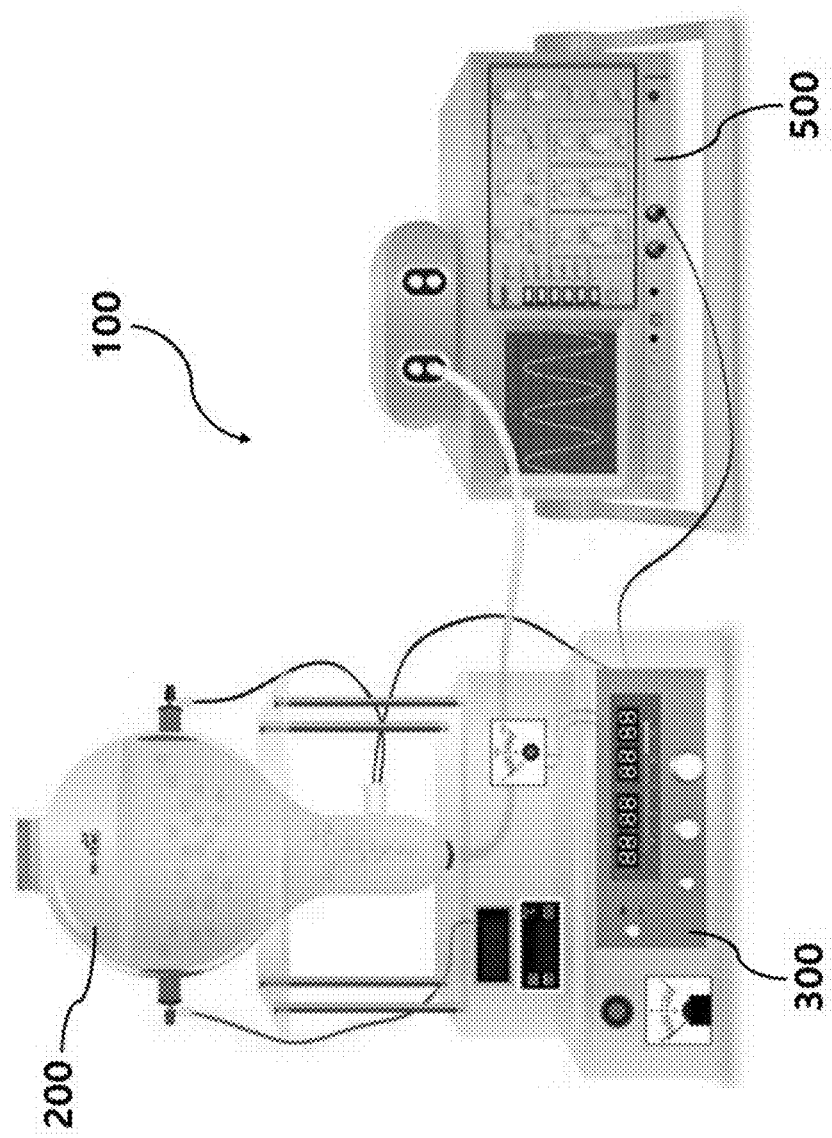
FIG. 7 is a reference photo showing an actual image of a radiofrequency cell incubator according to the present invention.

The amount of the secondary metabolites was remarkably increased by the radiofrequency process as compared with a case where the radiofrequency process was not carried out, and a profile of the secondary metabolites was analyzed by the HPLC. As a result of the analysis, it could be seen that daidzein and equol showed most remarkable results (FIG. 2). That is, it was observed that the amount of the daidzein was increased to about 5.4 times by the radiofrequency process. Further, it was observed that when the radiofrequency process was carried out with a radiofrequency of 240 kHz and power of 20 W 3 times every 5 minutes for a day repeatedly for two weeks, the amount of the equol as one of isoflavones was also increased to about 5.9 times (FIG. 4).

The present invention makes it possible to increase intracellular bioactive substances in various plant cells and thus can be used for development into various medicines, agricultural pesticides, spices, pigments, food additives, and cosmetics containing bioactive substances. Further, the present invention improves the conventional cell culture methods limitedly used for specific cells or specific metabolites for increasing amount of intracellular bioactive substances and thus can be widely applied to production of cells and secondary metabolites.

The present invention has been shown and described with reference to certain exemplary embodiments thereof. It will be understood by an ordinary person skilled in the art that the present invention can be modified and changed in form without departing from the spirit and scope of the present invention. Therefore, it should be considered that the disclosed exemplary embodiments are not intended to limit the present invention but intended to illustrate the present invention. The scope of the present invention is defined not by the above description but the appended claims, and all differences within the scope equivalent thereto should be construed as being included in the present invention.

What is claimed is:

1. A soybean placenta culture method for increasing amount of intracellular bioactive substances, the method comprising:
    (a1) a callus inducing step of culturing the soybean placenta in an MS (Murashige and Skoog) medium containing IAA (indole acetic acid), BAP (6-benzylaminopurine), sucrose, and gelite for 2 to 5 weeks for inducing a callus from a germinated plant;
    (a2) an adventitious root inducing step of culturing the callus in an MS medium containing IBA (indole-3-butyric acid), MES monohydrate(2-(N-morpholino), benzyladenine, sucrose, and gelite for 2 to 5 weeks for inducing an adventitious root from the callus; and
    (b) a radiofrequency processing step of processing the cultured soybean placenta with a radiofrequency for increasing amount of an intracellular bioactive substance in the plant cell,
    wherein the radiofrequency is used for processing is in a range of 240 to 270 kHz,
    wherein the radiofrequency is used for processing 3 times every 2 to 10 minutes per day repeatedly for 5 to 15 days,
    wherein the intracellular bioactive substances are daidzein and equol.

2. The method of claim 1, wherein the bioactive substance is at least one secondary metabolite selected from the group consisting of alkaloids, flavonoids, terpenenoids, glycosides, and metabolite pigments.

3. The method of claim 2, wherein the flavonoid as a secondary metabolite is at least one secondary metabolite selected from the group consisting of isoflavones, flavonols, flavanones, flavones, flavan-3-ols, and anthocyanins.

4. The method of claim 3, wherein the isoflavone is at least one secondary metabolite selected from the group consisting of daidzein, genistein, and equol.

* * * * *